United States Patent

Hersh

[11] Patent Number: 5,922,346
[45] Date of Patent: *Jul. 13, 1999

[54] ANTIOXIDANT PREPARATION

[75] Inventor: Theodore Hersh, Atlanta, Ga.

[73] Assignee: Thione International, Inc., Atlanta, Ga.

[ * ] Notice: This patent is subject to a terminal disclaimer.

[21] Appl. No.: 08/982,058

[22] Filed: Dec. 1, 1997

[51] Int. Cl.$^6$ .............................. A61K 47/00; A61K 9/68; A61K 9/28; A61K 9/44

[52] U.S. Cl. ................... 424/439; 424/440; 424/441; 424/464; 424/702; 514/2; 514/904

[58] Field of Search .................... 424/439, 440, 424/441, 464, 702; 514/904, 2

[56] References Cited

U.S. PATENT DOCUMENTS

| | | |
|---|---|---|
| 4,129,644 | 12/1978 | Kalopissis et al. . |
| 4,144,325 | 3/1979 | Voyt . |
| 4,224,339 | 9/1980 | Van Scott et al. . |
| 4,567,200 | 1/1986 | Tinti et al. . |
| 4,593,043 | 6/1986 | Tinti et al. . |
| 4,602,039 | 7/1986 | Cavazza . |
| 4,617,187 | 10/1986 | Okuyama et al. . |
| 4,710,489 | 12/1987 | Meister . |
| 4,769,382 | 9/1988 | Dubur et al. . |
| 4,818,521 | 4/1989 | Tamabuchi . |
| 4,839,159 | 6/1989 | Winter et al. . |
| 4,865,840 | 9/1989 | Burke et al. . |
| 4,895,727 | 1/1990 | Allen . |
| 4,895,840 | 1/1990 | Burke et al. . |
| 4,929,442 | 5/1990 | Powell . |
| 4,942,031 | 7/1990 | Levin . |
| 4,961,926 | 10/1990 | Gabrilove . |
| 5,008,119 | 4/1991 | Matsubara . |
| 5,023,235 | 6/1991 | N'Guyen et al. . |
| 5,032,384 | 7/1991 | Yeh et al. . |
| 5,075,102 | 12/1991 | Hubaud et al. . |
| 5,128,365 | 7/1992 | Spector et al. . |
| 5,290,605 | 3/1994 | Shapira ..................................... 424/439 |
| 5,290,809 | 3/1994 | Ippolito et al. . |
| 5,306,486 | 4/1994 | McCook et al. . |
| 5,330,757 | 7/1994 | Burke . |
| 5,378,461 | 1/1995 | Neigut . |
| 5,384,116 | 1/1995 | Pawelek et al. . |
| 5,397,770 | 3/1995 | Levin et al. . |
| 5,409,693 | 4/1995 | Perricone . |
| 5,418,253 | 5/1995 | Cavazza et al. . |
| 5,427,778 | 6/1995 | Finkenaur et al. . |
| 5,441,726 | 8/1995 | Mitchnick et al. . |
| 5,486,360 | 1/1996 | Ballagh et al. . |
| 5,494,924 | 2/1996 | Cavazza et al. . |
| 5,516,507 | 5/1996 | N'Guyen et al. . |
| 5,545,660 | 8/1996 | Grisar et al. ............................ 514/458 |
| 5,565,439 | 10/1996 | Piazza et al. . |
| 5,582,817 | 12/1996 | Otsu et al. . |
| 5,618,521 | 4/1997 | de Rigal et al. . |
| 5,626,883 | 5/1997 | Paul ......................................... 424/605 |
| 5,627,212 | 5/1997 | Cavazza et al. . |
| 5,667,781 | 9/1997 | Hersh et al. . |
| 5,667,791 | 9/1997 | Hersh et al. ............................. 424/401 |
| 5,696,109 | 12/1997 | Malfroy-Camine et al. ........... 514/185 |
| 5,709,873 | 1/1998 | Bar-Shalom et al. ................... 424/422 |
| 5,739,156 | 4/1998 | Bissett ..................................... 514/458 |
| 5,766,873 | 6/1998 | Noble et al. .............................. 435/25 |

FOREIGN PATENT DOCUMENTS

| | | |
|---|---|---|
| 0 516 901 A1 | of 0000 | European Pat. Off. . |
| 3542309 A1 | of 0000 | Germany . |
| WO 80/00427 | of 0000 | WIPO . |
| WO 94/13265 | of 0000 | WIPO . |

OTHER PUBLICATIONS

Balansky et al., "Modulation of the mutagenic activity of cigarette smoke, cigarette smoke condensate and benzo (a) pyrene in vitro and in vivo" (Abstract), Mutagenesis, vol. 9 (2), 107–112, 1994.

*Primary Examiner*—Shelley A. Dodson
*Assistant Examiner*—Marina Lamm
*Attorney, Agent, or Firm*—Malcolm B. Wittenberg

[57] ABSTRACT

A composition for reducing free radical damage induced by tobacco products and environmental pollutants. The composition includes reduced glutathione and a source of selenium. The composition can be administered orally in the form of a gel, lozenge, tablet or gum.

33 Claims, No Drawings

ANTIOXIDANT PREPARATION

TECHNICAL FIELD OF THE INVENTION

The present invention deals with the combination of several synergistic antioxidants, enzymatic co-factors and amino acids in appropriate delivery vehicles employed in solid carriers, such as tablets, lozenges and gums as a means of preventing and ameliorating signs and symptoms and complications to the oro-pharyngeal cavity and mouth including buccal mucosa, gums and tongue and the upper respiratory tract from damage caused by free radical species. Such free radical species are induced by tobacco smoke, smokeless tobacco, ingested or chewed noxious, malodorous or harmful substances and other inhaled environmental pollutants and particulate matter, including tobacco to secondary smokers.

BACKGROUND OF THE INVENTION

The deleterious effects of tobacco abuse are well known and regulatory agencies as well as the public constantly react to these scientific and epidemiologic evidences. Tobacco is indeed a worldwide public health hazard accounting for significant morbidity and mortality. Although smoking places an abundant oxidant insult to the oro-pharynx and respiratory tract, plus the local existing atmospheric pollutants in that specific environ, evidence cites the oxidant burden is on the entire organism of the smoker, particularly development or enhancement of atherosclerosis, causing cardiovascular disease, chronic obstructive pulmonary disease and various forms of cancer, including carcinomas of the mouth, pharynx, esophagus and lung.

Tobacco is a substance consisting of the dried leaves and stems of the plant *Nicotiana tabacum* which contains the drug nicotine, which is very addictive. The plant is native to North America but is now grown worldwide. Tobacco abuse has been identified as the single most preventable cause of disease, morbidity and mortality. Tobacco smoke contains many toxic chemicals and free radical species. There are three principal ways to consume tobacco: smoking, chewing and dipping and snuffing. 50 million Americans smoke and countless others are affected by tobacco smoke as secondary smokers. Children of smokers breathe this second-hand smoke and have more respiratory problems than children of non-smokers. Smokeless tobacco is used by as many as 12 million individuals and has a detrimental effect on the oral cavity plus systemic effects from buccal absorption of nicotine and other chemicals. Chewing looseleaf tobacco and "dipping" moist, ground snuff tobacco are common uses of tobacco without smoking. "Snuffing," that is, "snorting" dry powdered tobacco into the nasal passageways is rarely used in this country. Health risks from smokeless tobacco are still very significant and it is not a substitute for smoking.

Studies have estimated that tobacco smoke has over 3,000 different constituents, of which a number are toxic, some are carcinogenic and many generate free radical species. Most of these compounds have been identified in so-called mainstream and side stream tobacco smoke. The former is that volume of smoke drawn through the mouthpiece of the tobacco product during puffing while side stream smoke is that smoke emitted from the smoldering cigarette in between puffs. Although tar and nicotine are retained in the filter of cigarettes, this applies mainly to mainstream smoke, when comparing filter and non-filter cigarettes. Mainstream smoke emission is also markedly reduced both in low and in ultra low tar yield cigarettes. However, the emissions of toxic and carcinogenic components in side stream smoke are not significantly reduced in filter cigarettes when compared to non-filter counterparts. Thus, side stream smoke is a major contributor to environmental smoke, affecting both the smoker and their non-smoking counterparts, so called secondary smokers. The lower rates of consumption of cigarettes with high smoke yields has not reduced the indoor pollutants of carcinogenic substances and free radicals generating potential of tobacco smoke produced in side stream smoke, albeit their diminished levels in mainstream smoke by smoking low yield tobaccos and filter cigarettes.

Cigarette smoke induces oxidative damage to lipids, DNA and proteins, particularly protein-SH groups for this smoke contains high levels of both free radicals and aldehydes, including acetaldehyde (ethanol), propanol and acrolein, as well as other deleterious molecules.

In U.S. Pat. No. 5,060,672 (Oct. 29, 1991) which is herein incorporated by reference, Irimi and co-workers disclosed an efficient filter for tobacco smoke. Their mechanical and adsorptive filtering component also provided chemo sorptive properties to reduce aldehydes in the cigarette's smoke.

Tobacco, whether smoked as cigarettes, cigars or pipe or used as it is so-called smokeless or chewing modalities, causes common untoward effects in the oral cavity. Tobacco smoke has two chances to exert its deleterious effects in the mouth; when it is inhaled by the smoker and on its exit during exhalation. The American Lung Association states that chewing tobacco, whether one calls it snuff, a chaw, a plug, spit or smokeless tobacco is still a form of tobacco. The nicotine content is akin to cigarettes and this tobacco is etiologically responsible for oral cancer, just where it is chewed or "stored," in the mouth, cheek or gums.

Like cigarettes, evidence shows that cigars are also toxic and addictive. Cigar and cigarette smokers have a similar increased risk for oral and laryngeal cancers. While cigarette tobacco is generally flue cured with a resulting mildly acidic product, the slower curing methods for cigars render these mildly alkaline. At this pH, nicotine is more readily absorbed. Unlike cigarettes, cigars are less homogenous, and vary in size and nicotine content. Cigar smokers may spend an hour smoking a single large "Havana" although some actively inhale very little of this smoke; however, in non-inhalers, their nicotine levels may be elevated with no toxic co-absorption, as occurs in cigarette smokers. Cigar smokers also commonly hold an unlit cigar in the mouth, allowing further nicotine by local absorption. Thus, consumption of cigars may produce an equal or greater smoke burden of exposure and locally generate free radicals in the oral cavity which create deleterious effects and a risk of oro-pharyngeal disease. For cigars, as for pipe tobacco and smokeless tobacco, there is less available publicity and information for consumers than for cigarette smokers, although concomitant administration of synergistic antioxidant compositions of the present application may help prevent oral cancers and ameliorate oro-pharyngeal complications of tobacco abuse, whether from cigarettes, cigars, pipe or smokeless tobacco.

Cigarette smoke is divided into two phases, tar and gas-phase smoke. Cigarette tar contains high concentrations of free radicals. The most common oxidants include semi-quinone which is in equilibrium with hydroquinones and quinones, particularly in the viscous tar matrix. Many tar extracts and the oxidants, including the latter, are water soluble and reduce oxygen to superoxide radical which can dismutate to form $H_2O_2$. Importantly, glass-fiber type cigarette filters retain almost all of the tar particles that are larger than 0.1 micron. Thus, the filter acts as a trap for tars in cigarette smoke. There are an inordinately large number of free radicals, greater than $10^{15}$, in each puff in the gas-phase of cigarette smoke. While the oxidants in tar are stable, those organic radicals in the gas phase smoke are reactive carbon and oxygen centered radicals with extremely short half lives. Interestingly, concentrations of free radicals are maintained at high levels for more than 10 minutes and tend to increase as tobacco smoke is aged. It is thus considered that these gas phase smoke oxidants are in a steady state as they are both continuously formed and destroyed. The latter reactions are similar to those noted to occur in smog, pointing to the extra noxious stimuli to primary and secondary smokers in polluted atmospheric environments. Although the best protection from cigarette smoke oxidant damage is cessation of smoking with personal and "environmental" abstinence, antioxidant protection is rendered by oral solutions, sprays and aerosol administration, as taught by the present disclosure, and by supplemented dietary means, as suggested by some clinical investigations. These oral sprays and inhalatory measures would ameliorate and delay putative tobacco oxidant damage in smokers and their nearby non-smoking neighbors, as well as for those who use chewing (smokeless) tobaccos.

In addition to the above, in other in vitro studies gas phase cigarette smoke was assessed in its filtered and whole (unfiltered) states for oxidative effects on human plasma. Investigators noted the prevalence of lipid peroxidation in plasma after exposure to the gas-phase smoke, but not to the whole cigarette smoke. The reaction of lipid peroxidation did not commence until the endogenous ascorbic acid had been consumed, that is, vitamin C was oxidized completely. It was noted that cigarette smoke exposure caused oxidation of plasma protein thiols (methionine and cysteine amino acid linkages) and low density lipo-proteins. It was concluded that lipid peroxidation induced by the oxidants of gas phase smoke leads to changes in the lipoproteins associated with atherogenesis. As noted in this disclosure, the synergistic effect of reduced glutathione, selenomethionine and ascorbic acid or an ascorbic acid derivative are beneficial to combating tobacco oxidants and both ameliorating and delaying the effects of tobacco smoke on the oro-pharynx and the upper respiratory mucosa.

Cells subjected to oxidative stress may severely affect cellular function and cause damage to membrane lipids, to proteins, to cytoskeletal structures and to DNA. Free radical damage to DNA has been measured as formation of single-strand breaks, double-strand breaks and chromosomal aberrations. Cells exposed to ionizing radiation and cigarette smoke have also been demonstrated to have an increased intracellular DNA damage, a precursor of mutations and development of malignancies.

Macrophage cells and neutrophils have their phagocytic activity associated with the so-called "respiratory burst" reaction, which is dependent on plasma membrane NADPH oxidase activity. The resulting oxygen radicals may then be transformed to $H_2O_2$ by superoxide dismutase. Investigators have shown that smokers have a higher "respiratory burst" reaction of alveolar macrophages and peripheral neutrophils than non-smokers and the former also have higher incidence of oral and respiratory signs and symptoms than non-smokers. It was determined that there is a decrease of the effect of this "respiratory burst" reaction in smokers supplemented with oral mega doses of antioxidants. The intra-oral and inhalatory preparations of the present invention with synergistic antioxidants are thus beneficial to primary and secondary smokers.

Because of the oro-pharynx's access to the environment, like the skin to oxygen and ultraviolet radiation, the structures of the oral cavity may be damaged by inhaled, ingested or chewed noxious substances and gaseous and particulate materials, especially in both active and passive smokers, as well as injuries by systemic xenobiotics and by endogenous processes, such as inflammatory reactions. Reactive oxidizing species, as induced by inhaled tobacco smoke, ozone and nitrous oxide are important factors in generating free radicals and inducing inflammatory reactions. As in other tissues, antioxidant enzymes exist in the oro-pharynx and include superoxide dismutase (SOD), which converts superoxide to hydrogen peroxide and catalase which reduces hydrogen peroxide to water. This reaction may also be catalyzed by selenium as a cofactor to the enzyme glutathione peroxidase using reduced glutathione (GSH) as a substrate. GSH-peroxidases may also reduce lipid peroxides to the corresponding alcohols also using GSH.

Glutathione, a sulphur containing tripeptide (L-gamma-glutamyl-l-cysteine-glycine) is the most abundant non-protein thiol in mammalian cells and is recognized as the primordial antioxidant. Glutathione, in its reduced form, known as GSH, acts as a substrate for the enzymes GSH-S-transferases and GSH peroxidases (with selenium cofactor) that both catalyze the reactions for the detoxification of xenobiotic compounds and for the antioxidation of reactive oxygen species and other free radicals. GSH synthesis takes place in two steps:

(1) An initial rate limiting step catalyzed by gamma glutamyl cysteine synthetase to form gamma glutamyl cysteine.

(2) Glutathione synthetase catalyzes the reaction between glycine and glutamyl cysteine to form GSH.

Intracellular stability is conferred to GSH by the gamma glutamyl bond's resistance to intracellular peptidases. This bond may be cleaved by gamma glutamyl transpeptidase which is usually located on the external surface of cell membranes. Its activity is high in the kidney, where GSH is subject to renal clearance by tubular cells and by this transpeptidation reaction, resulting in urine excretion or retransport to plasma as the constituent amino acids, glutamine, cysteine, and glycine. In this pool, along with nutritionally derived amino acids from digestion and small bowel absorption, these amino acids are available to the liver for GSH synthesis. The liver and lung also export GSH in its oxidized form denoted as GSSG, which is produced when peroxides are detoxified by GSH peroxidase. GSSG is recycled back to the reduced form, GSH, by glutathione reductase in a reaction with NADPH.

The ubiquitous glutathione plays a vital function in maintaining the integrity of the reactive oxygen species-free radical sensitive cellular components. This is accomplished through its direct role as an antioxidant, in its reduced (GSH) form, as well as a cofactor as aforementioned. In cells, GSH concentrations for antioxidant activity are maintained in equilibrium by the enzyme glutathione reductase. Under states of GSH depletion, including malnutrition and severe oxidative stress, cells may then become injured from excess free radical damage and die.

Other non-enzymatic molecules playing an antioxidant role include the ascorbates (vitamin C) which, as free radical scavengers, also react with oxidized glutathione (GSSG) and reduce it to GSH. Also, in the lipid membrane of the cells, the hydrophobic alpha-tocopherols (vitamin E) act synergistically with vitamin C to inhibit lipid peroxidation, as may be induced by cigarette smoke, by actively scavenging lipid peroxides and other radicals.

Various studies have correlated the importance of oxidant stress to various organs resulting from tobacco smoke and other noxious environmental factors and thus continue to exert a toll on the public health of all countries. Significant morbidity and mortality result from smoking tobacco from cigarettes, cigars, and pipes and local oral pathology from chewing tobacco. Epidemiologic studies have strongly implicated tobacco in the pathogenesis of atherosclerosis and various malignancies, including oro-pharyngeal and respiratory tract neoplasias. Chronic cigarette smoking is associated with appearance of free radicals inducing oxidative damage. Measurement in blood, urine and tissues of various antioxidants or of by-products of free radical metabolic processes are supportive of tissue oxidant damage in the pathogenesis of various diseases associated with tobacco smoking and environmental pollutants.

In the oro-pharynx, cigarette smoke also accelerates the production of reactive oxygen species by recruiting local neutrophils and activation of phagocytic cells in response to the noxious agents. Attack by cigarette smoke and free radicals upon plasma proteins may be measured by carbonyl assay and by loss of enzyme activity and SH groups. Researchers have shown that whole and gas phase cigarette smoke elicit formation of carbonyl in human plasma, which is particularly inhibited by GSH. In contrast, exposure of human plasma to gas phase but not to whole cigarette smoke produces oxidative damage to lipids.

Leukoplakia, a tobacco induced white patch on the buccal mucosa, as found in smokers, is a localized irritation due to direct contact of smoked or smokeless tobacco and it is directly related to the frequency and years of tobacco abuse. Although leukoplakia is a benign oral lesion, it has a malignant potential, requiring a biopsy of the lesion to rule out cancer. Leukoplakia may regress or resolve completely when use of tobacco products is discontinued. Adequate oral examinations by primary physicians and dentists is paramount to reduce smoke induced mouth and teeth pathology.

In addition, tobacco contributes to other oral symptoms or pathologies of the mouth and teeth. Tobacco may cause halitosis, may numb the taste buds, and interfere with the smell and the taste of food. It may stain teeth and contribute to dental caries. Smokers have more dental tartar (calculus) than non-smokers. Tobacco is associated also with destructive periodontal (gum) disease and tooth loss. Acute necrotizing ulcerative gingivitis ("trench mouth") is a destructive, painful inflammatory condition occurring mainly in cigarette smokers. Swelling of the nasal and sinus membranes have also been associated, purportedly, in individuals who are "allergic" to tobacco smoke.

Besides leukoplakia, another generalized whitish hue on the buccal mucosa represents the entity of oral submucous fibrosis. This disease occurs mainly in India and is a chronic, progressive premalignant condition. The etiology is chronic chewing of tobacco or areca nut or both. The fibrosis results in restriction of mouth opening and involves the palates, tonsillar fossa, buccal mucosa and underlying muscle. Associated with this condition is also oro-pharyngeal carcinomas, also with a high frequency in India and associated in 70% of cases with chewing tobacco. Smokeless tobacco and areca nut usage is also common in Pakistan, Bangladesh and Java and in these and Indian immigrants to the United States and United Kingdom.

Over 30,000 new cases of cancer of the oral cavity are diagnosed annually, accounting for two to four percent of all new cancers. Oral cancer kills 8,000 patients each year and only half of cases diagnosed annually have a five year survival. The great majority of these patients are users of tobacco products. Other risk factors include alcohol abuse, nutritional deficiencies and poor oral hygiene.

Research has recently linked benzopyrene, as in cigarette smoke, with mutations to the human P53 gene leading to oral and respiratory malignancies. Notably, 3, 4-benzopyrene is present in polluted atmospheres of large cities such as Los Angeles, Mexico City, and London, emanating as an exhaust product of motor traffic, especially diesel engines. Breathing contaminated air with high concentrations of this compound, particularly under foggy conditions as in London, provides more than 100 times as much of this putative mutagen than for a heavy cigarette smoker. Thus, the use of the present invention as taught herein would be most beneficial to citizens, particularly if they are also smokers, of congested cities with much traffic and with smog and fog. This provides to the individual another protective measure to such free radicals and mutagens generated in their bodies, not withstanding important measures to decontaminate the atmospheric pollutants and public health and personal efforts at tobacco cessation.

Cigarette filters "trap" nicotine tars but not the gas phase compounds. Epidemiologic studies have been done in various countries to show the differential effects of tar content, amount of cigarettes smoked, type of tobacco smoked, and use of filters on oro-pharyngeal and pulmonary cancer risk in cigarette smokers.

Cigarette smoke has untold effects through free radicals and other mechanisms of affecting other organs, such as the skin. Dr. Douglas Model of England in 1985 added to the medical lexicon the term "smoker's face" from a study with pictures of 116 cases and suitable non-smoking controls. Akin to photodamage, those with smoker's face appear older and have more wrinkles. They also have a greater frequency of cancers of the lips and mouth.

Recently, sales of cigars have risen, partly due to their gaining popularity with women and the advent of the female friendly "cigar bar." Evidence, however, exists that cigar carcinogenic particles exceed those of three cigarettes and the level of carbon monoxide is 30 times greater. Fumes from cigars are of greater consequence to secondary smokers. Epidemiologic studies reveal greater frequencies of heart disease, emphysema, and cancers of the mouth and pharynx in cigar smokers when compared to matched non-smokers.

There are a number of preparations on the market as dentifrices, gels, breath fresheners and mouthwashes and oral rinses to protect the mouth and teeth from the effects of chewed or smoked tobacco. Cigarette tar may deposit on the teeth, gums, tongue and other surfaces of the oral cavity of smokers. Tobacco tar, a dark, oily, viscid blend of polycyclic aromatic and aliphatic hydrocarbons, is produced in cigarettes, cigars, or pipe smoke by the burning of the tobacco. The smoker inhales the tar and other tobacco smoke combustion products are sucked into the oral cavity and respiratory passages. The smoke is then exhaled, passing a second time through the mouth of the smoker, anew depositing tar. This causes discoloration of the teeth and other oral surfaces. Not only may there be smoker's "bad breath" but also tooth decay and gum disease. Smokeless tobacco is equally locally deleterious. Food particles, oils and other substances may also be deposited on mouth surfaces. The tars and mainstream smoke will elicit free radical and inflammatory responses in the mouth and other mucosal surfaces. The antioxidants and reparative preparations of this invention may be prepared as oral and dental compositions as well as with optional added ingredients that are also breath fresheners, fluorides, anti-microbials, and solubilizers of tars and essential oils. Most of the dental products used as "anti-tobacco" are in the form of toothpastes and gels.

Diamond patented a combination of non-ionic and anionic surfactants with at least one essential oil as dental and oral preparations for smokers for solubilizing and removing tobacco tars as well as onion and garlic essential oils. U.S. Pat. No. 5,514,366 (May 7, 1996), herein incorporated by reference, teaches complimentary uses of the preventive and reparative effects of the present invention.

GSH has been shown to have multiple functions in detoxification and its depletion in extracellular fluids and cells is associated with an increased risk of chemical toxicity. Although there are large variations in dietary sulphur amino acid content, these variations do not correlate with GSH levels in the blood plasma pool. These GSH levels, however, do vary with age, race and gender of human subject and with dietary habits and intakes. Investigators have reported that extracellular pools of GSH, including plasma, respiratory tract lining fluid and oral and small intestinal lumen are GSH vital protectants against chemically induced injury. These would include the chemicals in tobacco smoke and other environmental pollutants as well as chemicals in smokeless tobacco preparations and other chewable or orally ingested substances. The aforementioned pools, through GSH and related synergistic antioxidants, as proposed in the present invention, detoxify chemicals extracellularly, supply GSH and its precursor amino acids to cells and protect the extracellular surface of the plasma membrane from damage. Alterations in GSH status could thus alter this regulatory function by GSH and thereby lower the threshold for chemically induced cell death by apoptosis, making GSH both a useful protectant to and biomarker for risk from a variety of single or mixtures of deleterious chemicals, such as in various types of tobacco.

Some mammalian cells are able to absorb intact the tripeptide glutathione. It may also be synthesized by some organs, particularly the liver. Various scientific papers have addressed a method for proper replacement of glutathione, particularly to increase cellular levels in glutathione depleted states. Certain diseases cause glutathione depletion from interaction endogenously with metabolic intermediates, the various deleterious free radical species. Labeling glutathione, at the intracellular level as the "antidote physiologically appointed to the neutralization and thus detoxification, by the formation of covalent bonds, of highly reactive toxic substances of endogenous or exogenous origin," Pilotto and coworkers patented dipeptide compounds with pharmaceutical properties to replete the body's glutathione levels. Their U.S. Pat. No. 4,761,399 dated Aug. 2, 1988, teaches raising glutathione levels by various routes, including oral, inhalation and parenteral methodologies. Meister, in U.S. Pat. No. 4,710,489 issued Dec. 1, 1987 teaches new molecules to increase cellular levels of glutathione. The invention of the '489 patent deals with using pure alkyl mono-esters of glutathione, wherein the ester is a glycine carboxylic acid. These molecules may be administered orally or by injection.

It is thus an object of the present invention to provide various compositions and methods of employing such compositions for preventing and ameliorating signs and symptoms and complications to the oro-pharyngeal cavity and mouth including buccal mucosa, gums, teeth and tongue as well as the upper respiratory tract as a result of tobacco oxidants and other gaseous and particulate matter pollutants.

These and further objects will be more readily appreciated when considering the following disclosure and appended claims.

SUMMARY OF THE INVENTION

The present invention is directed to a composition of synergistic antioxidants and the use of this composition employed in a gum, tablet or lozenge delivery systems to prevent and ameliorate free radical damage induced by smoking and environmental pollutants to the structures of the oro-pharynx and upper respiratory tract. Active ingredients include reduced glutathione, selenium as an element or as a seleno amino acid like selenomethionine and optionally the sulphur-containing amino acids L-cysteine and N-acetyl-L cysteine and/or L-methionine. As further optional ingredients, the composition contemplates the use of ascorbic acid and/or its derivatives, alpha-tocopherols and/or its derivatives. Depending upon the target organ and additional disease states or conditions encountered, other anti-oxidants or molecules may be included in these preparations. These include, but are not limited to, the enzyme superoxide dismutase, vitamin A and/or beta-carotene, zinc and fluoride compounds.

DETAILED DESCRIPTION OF THE INVENTION

Antioxidants have been found to inhibit all stages of carcinogenesis whereas other antioxidants are more specific and thus more effective against tumor initiation or promotion or tumor progression. Glutathione and selenium have been shown to play prime roles in protection of carcinogenesis and also in preventing other cancers, when selenium is taken orally thereby replenishing selenium body stores.

Likewise, glutathione, inhibits carcinogenesis, and indeed when its concentration is suppressed by chemicals so that glutathione levels are significantly lowered, chemical carcinogenesis is enhanced and progression of tumor numbers and tumor size increases. Reducing the intracellular levels of GSH in cells increases their sensitivity to oxidant damage. Studies have shown that increases in intracellular GSH are beneficial. An L-cysteine delivery agent not only enhanced endothelial cell GSH concentration, but also protected these cells from damage from endogenous hydrogen peroxide. This preventive role of GSH is of significant biologic value. Without being bound to any particular theory, it is noted that reduced glutathione is employed in protecting cells against oxidative stress by itself being oxidized. Thus, L-glutathione must act in combination with other enzyme systems in order to be reduced so that it may renew its role as a free radical scavenger. GSH functions also coordinately with the enzyme glutathione peroxidase which requires selenium as a cofactor to exert its biologic antioxidant function. Selenium compounds have been shown to scavenge oxygen-centered radicals in vivo with reduced glutathione through glutathione peroxidase. It is believed that selenium-GSH peroxidase catalyzes toxic hydrogen peroxidase in the presence of reduced glutathione. This reaction reduces glutathione to oxidized glutathione GSSG. In turn, the GSSG is reduced back to GSH by the enzyme GSH reductase thereby maintaining abundant cellular GSH to scavenge free radicals anew.

In summary, the major functions of reduced glutathione (GSH) in protection against lipid peroxidation are related to three types of reactions, all inter-related and synergistic in combining non-enzymic scavengers and enzymic and dietary provided antioxidants.

1. GSH with selenium co-factor glutathione peroxidases eliminate toxic peroxides.
2. GSH reduces oxidized forms of vitamin C which, in turn, maintains vitamin E in its reduced form promoting its metabolic functions. Thus, GSH supports the free radical reductions and free radical chain-terminating functions of the two nutrient antioxidants, vitamins C and E.

3. GSH functions through glutathione S-transferases to detoxify reactive aldehydes created during the process of lipid peroxidation.

As noted too, some cells have sodium dependent up-take systems for GSH, allowing cells to use both exogenous GSH and endogenously synthesized GSH, thereby enhancing a cell's ability to survive oxidative and free radical species damage. In this fashion, extra-cellular GSH also protects cells' survival.

Investigative studies have shown that cells' viability correlates best with content of GSH in mitochondria. In the absence of GSH, lipid peroxidation is uncontrolled and leads to cell injury and death. Conversely, GSH protects cells from the ravages of free radicals, working synergistically with the antioxidant enzymes and the dietary vitamin antioxidants.

For those in the chicle or gum industry, the compositions of the base for both sugar containing chicles and reduced calorie chewing gums and bubble gums are well known. The present invention can be used with reduced calorie gums, particularly with the polyols xylitol and sorbitol, but this invention is not restricted to these sweeteners. These chewing gums generally contains 20–30% of a water insoluble gum base, and from 30 to 90% of a filler or texturizing agent (called bulking products). Water soluble flavorings are also added. The gum base may also contain plasticizers or softeners to improve the consistency and texture of the gum. Some of these chicles are saliva stimulating chewing compositions with specific salivary stimulants. One such composition is taught by Cherukuri et al. in U.S. Pat. No. 4,980,177 dated Dec. 25, 1990, which is herein incorporated by reference.

Another method for the application of the active ingredients of this invention in the chewing gums, bubble gums, lozenges and tablets is to incorporate the various antioxidants, minerals and amino acids in liposomes or other state of the art encapsulating vehicles, akin to nanospheres, glycospheres and others as used in topical compositions. Liposomes are lecithin spheres that form an oil protective membrane around the putative active ingredients of these compositions. These carriers also deliver the active ingredients locally for their preventive and therapeutic functions as well as systemically through buccal mucosal absorption. Unger and co-workers have taught therapeutic drug delivery systems comprising gas-filled liposomes which encapsulate the active preparation in U.S. Pat. No. 5,580,575 dated Dec. 3, 1996, which is herein incorporated by reference. Earlier, Chakrabarti et al. and U.S. Pat. No. 5,5380,531 dated Jan. 10, 1995 which is also herein incorporated by reference, disclosed preparations comprising a lipid and a modified peptide for encapsulating amino acids into liposomes.

As noted above, xylitol is contemplated for use herein as a sweetener to mask the taste of the present active ingredients. Xylitol chewing gums have been evaluated in various field studies for their ability to influence the rates of dental caries in children. Makinen and co-workers did a 40 month double blind cohort study of nine treatment groups, including various doses of xylitol, on the relationship between the use of these chewing gums and the development of cavities. The study was performed in 1989–1993 in Belize on 1,277 children. They showed significant reductions in rates of dental caries in xylitol treated groups, compared with the no-gum chewing group and concluded that the systematic usage of polyol based chewing gums reduces the frequency of cavities, with xylitol chicles being even more effective than sorbitol gums. Other studies have also revealed that high content xylitol confections, including candies and chewing gums are not only non-cariogenic but also inhibit caries.

As a further preferred embodiment, the current application contemplates coating chewing gums with at least some active ingredients to prevent dental caries and dental plaque, like the aforementioned xylitol sweetener and flavors plus anti-halitosis compounds, line zinc salts, to act as breath fresheners and to combat oral malodor. The synergistic complex of antioxidants will be paramount and include, as stated, at least approximately 0.5 mg L-glutathione, 5 mcgm selenium as selenomethionine and optionally 15 mg vitamin C and 10 IU vitamin E to neutralize and scavenge free radicals in the oral cavity. Other optional ingredients include superoxide dismutase, vitamin A, beta-carotene, the amino acids cysteine, methionine, taurine, and/or arginine, as well as zinc salts, such as zinc acetate or zinc gluconate. The substances incorporated in the gum are released in the mouth to exert their beneficial effect during the process of mastication. The active ingredients may act locally and may also be absorbed through the buccal mucosa for systemic use.

Hill in the '530 patent summarizes referenced patents which deal with chewing gums which provide flavors and which deliver active substances into the oral cavity. For example, U.S. Pat. No. 3,075,884 teaches the mixing of active ingredients in corn syrup which is coated unto a gum. U.S. Pat. No. 3,011,919 teaches a method for incorporating actives by providing coatings with wet sugar. U.S. Pat. No. 3,352,689 discloses formulations of a sugarless gum, also to release actives in the mouth.

Hill's '530 patent also discloses a number of references dealing with chewing gum compositions containing anti-plaque properties. In addition, Hill also teaches the use of xylitol and sorbitol in chewing gums.

Westall et al in U.S. Pat. No. 3,821,417 dated Jun. 28, 1974, which is also herein incorporated by reference, discloses the use of dihydrochalcone as well as the use of various antioxidants in chewing gums, namely butylated hydroxyanisole, butylated hydroxytoluene and propyl gallate.

Although the chewing gums and bubble gums of this invention will preferentially be reduced-calorie compositions, the present invention may optionally include compositions with metabolizable sugars. These chewing gums compositions are well known in the industry and can include a gum base (about 40% to 60% by weight of the composition), which comprise an elastomer, a polyvinyl acetate polymer, an acetylated monoglyceride, a wax with melting point below 60 degrees C., an elastomer solvent, plasticizer and a filler. The gum is then provided with the present synergistic antioxidant complex so that each piece of gum has approximately at least 0.1 mg L-glutathione, 2.0 mcgm selenium as selenomethionine, 10 mg ascorbic acid, 2.5 IU vitamin E and 1.0 mg L-cysteine or 1.5 mg N-acetyl cysteine. It is noted that the reduced calorie gum could contain xylitol or lactitol as the sweetener while the standard calorie gum will have sucrose, lactose or other mono-or di-sacharides, plus flavoring agents. Chewing gums may in addition contain saliva stimulating compounds, usually organic acids, such as described by Cherukuri et al. in their '177 patent.

As optional embodiments, other ingredients may be added such as breath fresheners and breath cleansing (anti-halitosis) agents. Plevy taught in U.S. Pat. No. 4,740,368 dated Apr. 26, 1988, which is herein incorporated by reference, compositions with amylase as breath cleansing confections. Alpha amylases are synthesized by the salivary glands and exocrine pancreas and are able to digest carbohydrates. Plevy's preparation used 1–8-skb units of alpha-amylase of fungal origin to degrade starch. Along with artificial sweeteners and flavoring, this enzyme is the main ingredient of comestible confectionary bases, such as gums and lozenges. Separately, Pera in U.S. Pat. No. 4,775,525 dated Oct. 4, 1988 which is also herein incorporated by reference teaches a dental formulation containing sodium alginate. It is used as a calcium chelating agent which weakens the bond between the plaque and the teeth. The referenced patent advocates the concomitant use of benzalkonium chloride and zinc.

In addition to providing these synergistic anti-oxidants in standard chewing gums, alternatives to chicle gum is contemplated. Conventional chewing gums are not digestible or biodegradable and cause on disposal unsightly litter. Thus, gum base substitutes which are edible have been the object of various teachings. For example, U.S. Pat. No. 5,366,740 by J. J. Shaw dated Nov. 22, 1994, which is herein incorporated, uses a wheat gluten preparation as an edible "chewing gum". Its manufacture includes calcium carbonate, glutinous rice flour, and ascorbic acid as softeners of the wheat gluten, as well as other ingredients commonly used as wheat flour dough conditioners. If used herein, such a chewable gum would also provide the present synergistic anti-oxidants application to the oral mucosa to combat tobacco smoke, chewing tobacco or other environmental ingested or inhaled pollutants which all induce free radicals. The edible gum may also have breath fresheners. All the components of this chewable gum, distinct from commercially available "chewable tablets" may then be swallowed while its protein and carbohydrate bases are digested. All residual vitamins, minerals, and amino acids not absorbed by the buccal mucosa during the process of chewing will be swallowed and then made available systemically to the body following their intestinal absorption. This would be akin to the aforementioned constituents in conventional chewing gums which are swallowed dissolved or dispersed in saliva.

When the present invention is in the form of gels, lozenges, gums, candy, chewable tablets, or chewing gums, flavoring may be added. Flavors may be based on oils of spearmint and peppermint. Other flavoring materials may include menthol, clove, cinnamon, wintergreen, citrus fruits, eucalyptus, aniseed and others which are commercially available. Flavors may range in concentrations depending on the product from about 0.1 to about six percent by weight of the total composition.

When the products are in a form of gels, bicarbonates may be present in the composition with thickening agents, in a concentration from 0.5 to 5.0% by weight. State of the art thickeners with a bicarbonate and zinc salts, include, but are not limited to chicle, xanthan, arabic, karaya or tragacanth gums. Alginates, carrageenans and cellulose derivatives such as sodium carboxymethyl, methyl, or hydroxyethyl compounds can also be included, as well as surfactants and abrasives. In order to decrease dental cavities and add flavor, without using metabolizable sugars, sweetening agents as saccharin, sodium cyclamate, sorbitol, aspartamane, and others may be used in concentrations from 0.005 to 5.0 per cent weight of the total composition, although, as stated xylitol is the preferred sweetener.

Researchers in Finland showed that chewing gum containing the natural sweetener xylitol reduced chronic ear infections in children. Xylitol, a five carbon sugar alcohol, found in birch and maple trees and corncobs, also has been used to fight tooth decay, since local mouth bacteria cannot digest this sweetener. It appears that xylitol prevents bacteria from attaching to cells in the posterior area of the mouth from whence they could enter the ear passages and cause infection. Xylitol is of value for oral hygiene since it is not metabolized by mouth bacteria so that organic acids which attack teeth are not produced. Xylitol reduces dental caries and reduces the amount of plaque-forming bacteria (streptococcus mutans) in the mouth. Various clinical studies in other countries have confirmed the unique dental benefits of xylitol, thus it is of particular use in pediatric mellitus. Therefore, xylitol preferably will be used as a sweetener in these compositions, particularly in the chewing gums and lozenges of the present invention for its known noncaloric, salutory oral and dental effects.

Lactitol may also be used as a substitute for sucrose in sugar-free compositions of the present invention. Lactitol is a disaccharide sugar alcohol derived from lactose, highly water soluble and of low hygroscopicity, making it a suitable non-caloric sweetener for use in tablets and other solid dosage forms.

A number of compounds may be added to the present chewable tablets, lozenges, candies and gums in order to enhance their aromas or tastes. These substances may also impart fragrances to the aforementioned. Grapefruit and citrusy aroma and flavors have been included in smoking tobacco articles both prior to smoking and on smoking in both the main stream and the side stream smoke. Methyl phenyl pentanol derivatives have been used to augment and enhance aromas, such as in perfumes and colognes. Schreck patented these derivatives for use in tobaccos and tobacco articles as taught in U.S. Pat. No. 4,458,699 dated Jul. 10, 1994, which is herein incorporated by reference. Floral, green, weedy, fruity, minty, citrusy, oriental and green-pepper-like aroma and taste nuances are well known to those skilled in the art of flavors and fragrances which can be used in the present oral compositions including chewing gums, bubble gums, chewable tablets, lozenges and candy.

Flavored hard tablet and lozenges prepared pursuant to the present invention are made with the recommendation that the user dissolve them so that the ingredients are both delivered to the oral cavity and remaining molecules, not absorbed by the buccal mucosa, will be admixed with saliva and swallowed normally. Candy in the form of tablets with various flavors and the sweetener xylitol are manufactured using state of the art technology as known in the confectionary industry. These tablets are intended to carry the above described synergistic complex of antioxidants. For example, one such tablet can have the following ingredients in amounts as recited:

4 (four) tablets equal the following dosage per day:

| | |
|---|---|
| L-Glutathione | 40 mg. |
| Selenomethionine | 25 mcgm |
| Ascorbic Acid (Vitamin C) | 30 mg. |
| Alpha Tocopherol (Vitamin E) | 15 IU |
| Retinyl Acetate (Vitamin A) | 2500 IU |
| L-Cysteine | 10 mg. |

Lozenges may be "flavored" with standard therapeutic agents such as methol, eucalyptus, and ingredients known in the "cold products" industry.

The components of the present synergistic antioxidant complex may also be incorporated into chewable flavored tablets. Such chewable tablets may be enhanced with sugars like sucrose, fructose and/or lactose. Alternatively, artificial sweeteners, such as xylitol, lactitol, sorbitol and the like can be used herein. Natural flavors such as citrus fruits, cherry, strawberry, grape, and the various mint flavors, to name a few, can be incorporated in chewable tablets of the present invention. Inactive ingredients, as vehicles for these flavorings include dextrins, starch, silica, gelatin, hydrogels, magnesium stearate and phosphate, glycerides of stearic and palmitic acids, and usual fillers and thickeners as commonly employed in chewable tablets and vitamins, such as are commercially available.

Serving sizes of these chewable tablets may vary so that a consumer can ingest from one to four chewable tablets per day. The active ingredients contained within the tablet can be varied so that in consuming the recommended number of tablets, usually from one to four, the user will ingest the recommended or minimum daily requirement of the active ingredient as prescribed by dietary supplement guidelines.

For example, a chewable tablet designed as a two a day dosage (morning and evening) would have the following active ingredients:

| | |
|---|---|
| L-Glutathione | 20 mg. |
| Selenomethione | 25 mcgm |
| Ascorbic Acid (Vitamin C) | 30 mg. |
| Alpha Tocopherol (Vitamin E) | 15 IU |
| Retinyl Acetate (Vitamin A) | 2500 IU |
| L-Cysteine | 10 mg. |

To this tablet, one could also include xylitol or lactitol as the sweetener with flavorings according to taste.

In a most preferred aspect of the present invention, the aforementioned oral or inhaled pharmaceuticals, amino acids and active antioxidant containing composition has a formulation for total daily consumption to include recommended daily allowances of reduced L-ascorbic acid, tocopherols, and other vitamins. In addition to L-glutathione, the preferred selenium dosage is approximately at least 10 mcgm of elemental selenium per day most preferably 25 mcgm per day. This may also be used as selenomethionine, which is commercially available in a 0.5% trituration with dibasic calcium phosphate. This fine powder contains from 5,000 to 5,300 mcgm of selenium per gram of the selenomethionine preparation. The compositions may also have about 30 IU of D,L-alpha tocopherol and about 1000 mcgm of vitamin A, as the retinol equivalent or 5,000 units as vitamin A with a range of 20–40% beta carotene. These are recommended daily allowances and these active ingredients may be administered in oral liposomes, either each encapsulated alone or in combinations. Knight and co-workers in U.S. Pat. No. 5,049,388 (Sep. 17, 1991), incorporated herein by reference, disclosed small particle aerosol liposomes. These particles had diameters less than 5 microns. Medications were combined with the liposomes such that the drug or active ingredient interacted with the liposome membrane.

The aforementioned compositions may be particularly useful in the prevention and treatment of tobacco smoke or other gaseous or particulate matter exposure, including buccal damage from chewing tobacco. They represent a delicate balance of ingredients which serve not only to reduce the number of free radicals but also to inhibit the tissular metabolic oxidation. The more preferred formulations in accordance with the present invention also enhance the performance of the composition by recycling certain antioxidant ingredients in the formulation after these are absorbed and by offering the formulation allowing for long term use. These compositions when provided in sufficient dosage over a period of time may be useful in the treatment and the prevention of the damage caused in the oropharynx and upper respiratory tract, by exposure to tobacco smoke, smokeless tobacco and other environmental pollutants.

Glutathione and selenium act synergistically in vivo as they are both constituents of the same enzymatic system. GSH serves as a specific donor substrate while selenium, provided from alimentary sources or locally from topically administered preparations of selenium, selenoamino acids or selenium yeast extract, provides the prosthetic group of GSH peroxidase. The glutathione and selenium antioxidant functions are intrinsically related since by keeping a peroxidase in action, the GSH and selenium, contribute to the removal of the dismutation product of free oxygen radicals, namely, hydrogen peroxide. In a broad sense, GSH and selenium modulate free radical chains initiated or sustained by hydroperoxides. Selenium is used in the present invention for its role as an antioxidant as well as its anticarcinogenic and antimutagenic properties. Thus, selenium-glutathione complex may lower the level of potentially damaging peroxide radicals that are generated from various carcinogenic promoting chemicals, including tar phase and gas phase tobacco smoke inhaled by-products, particularly side stream smoke.

Glutathione peroxidase, a group of water soluble enzymes, also catalyze the destruction of both aqueous and membrane-bound hydroperoxides. In dietary selenium deficiency, these enzyme levels are markedly decreased resulting in severe free radical damage to the tissues so involved. The other related antioxidant systems cannot make up for depressed local activity of selenium and selenium dependent enzymes. Thus, the importance of providing selenium in these intra-oral antioxidant preparations, as well as ascertaining adequate nutritional supplements. Selenium may be provided as a selenoamino acid, like selenomethionine, as such, is protected in oral liposomes.

L-ascorbic acid (vitamin C) or its derivatives can be employed in these compositions primarily for their antioxidant activities. Stabilized vitamin C is employed so that it does not lose its physiological reducing activities because of its high susceptibility to oxidation. The minimum daily requirement for adults has been established. It appears, however, that cigarette smokers need supplemental vitamin C. Vitamin C, as an antioxidant, has been employed in vitamins, beverages, foodstuffs, pharmaceuticals and cosmetic preparations. Vitamin C has also been used for the prevention of viral diseases and a preventative by its antioxidant properties of development of cutaneous premalignant lesions and malignant tumors. Sakai, et al in U.S. Pat. No. 5,508,390 (Apr. 16, 1996) have outlined uses of an L-ascorbic acid. Such stabilized vitamin C is used as an additive in various preparations. The emphasis of this preparation of ascorbic acid is in its stabilizing and reducing function. Todd, Jr., in U.S. Pat. No. 5,084,293 (Jan. 28, 1992), describes a method of using "activated" ascorbic acid preparations with antioxidant compositions. These include anhydrous compositions to embody propylene glycol or non-ionic surface-active agents to provide vitamin C with increased antioxidant activity in fats, oils, and carotenoids.

Vitamin C, ascorbic acid, plays a major role in human metabolism. As an antioxidant, it protects the skin from free radical damage induced by radiation, tobacco smoke, and other inhaled or swallowed environmental pollutants. Vitamin C promotes collagen synthesis, tissue repair and wound healing. Vitamin C also renders important protection against damaging chemicals associated with cigarette smoking, including nicotine, carbon monoxide, nitrogen oxides, nitric acid gas and others. Although ascorbic acid may be reduced in this scavenging role, the ascorbate radical may then be removed by the NaDPH enzyme systems as sources of reducing molecules. Thus, vitamin C may be recycled to abate or lessen the process of lipid peroxidation by its synergistic function with others. Markham in U.S. Pat. No.

4,822,891 refers to the oral administration of vitamin C to demonstrate its free radical attributes. Others have shown that chronic tobacco smokers had higher urinary levels of 8-EPI-prostaglandin F2A than non-smokers. Oral supplementation with vitamin C suppressed urinary levels of this metabolite, suggesting a reduction of oxidant stress in these subjects.

Cigarette smokers often have lower plasma levels of ascorbic acid than matched non-smoking controls. Clinical and investigative evidence suggests that smokers may have a higher ascorbic acid requirement and that supplementing dietary vitamin C may be protective to the smoker. In vitro studies have shown that antioxidants and reducing substances may prevent the removal of elastase inhibitor capacity induced by cigarette smoke.

Other components were also investigated as being useful in practicing this invention, for example, the sulphur containing amino acid cysteine is one of the three amino acid constituents of the tripeptide antioxidant glutathione. Studies have shown that cysteine and cysteine derivatives, as recited in U.S. Pat. No. 4,910,222 by Puricelli, have liquefying and expectorating properties. These compounds may be administered by the oral route as a solid (capsules), or as a liquid (emulsions) and by aerosol sprays.

Vitamin A is an essential nutrient. Relative vitamin A deficiency may adversely affect the skin and mucous membranes, including the mucosa of the oral cavity. These alterations are reversible on repletion with vitamin A or one of its derivatives.

Xylitol, the sweetest of all bulk sugar substitutes, tastes like sugar, leaves no aftertaste, and has 40% less calories than sugar. A caloric value of 2.4 kcal/gram is accepted for nutritional labeling. This five carbon sugar alcohol has a negative heat of solution which causes a cooling effect when it dissolves in the mouth, particularly concomitantly using mint flavors. When sugars are ingested, the micro-organisms in the mouth ferment the sugars with a consequent drop in pH, even to a low pH of 4. When the contents in the mouth are acid, there is demineralization of tooth enamel. Stimulated flow of alkaline saliva is then necessary to return the pH in the mouth to normal levels. Thus, use of xylitol reduces susceptibility to dental caries by helping to remineralize affected teeth and by inhibiting demineralization of healthy teeth. Studies have also shown that adults chewing xylitol gum or xylitol/sorbitol gums or mouth rinses develop significantly less dental plaque than controls chewing sucrose gums. Their dental plaque too showed an improvement in the ability to resist any drop in pH. In the xylitol groups, studies show that xylitol inhibits the growth of various oral cariogenic bacteria, particularly those of Streptococcus mutans.

Although the susceptibility to dental caries is influenced by various factors including diet and eating patterns, tooth surface and salivary rates are also important. The resistance of the enamel and dentine may be increased by regular exposure of the teeth to fluorides systemically. This is accomplished via drinking water and fluoride tablets or topically via toothpaste, gels and mouthwash. Various studies have demonstrated that consumption of even small quantities of xylitol enhances the beneficial effects of existing fluoridation program, resulting in reduction in new caries. Similar trends have been observed when xylitol is applied topically such as a mouth rinse.

When the present preparations are in the form of gums, tablets or lozenges, flavorings may be added to these compositions, as per the state of the art in these respective industries. Flavors may be based on oils of spearmint and peppermint. Other flavoring materials may include menthol, clove, cinnamon, wintergreen, citrus fruits, eucalyptus, aniseed and others commercially available for these flavoring purposes.

Flavors may range in concentrations depending on the product from about 0.1 to about 6.0% by weight of the total composition.

When the products are in a form of gel, bicarbonates may be present in the composition with thickening agents, in a concentration from 0.5 to 5.0% by weight. State of the art thickeners with bicarbonate and zinc salts include, but are not limited to chicle, xanthan, arabic, karaya or tragacanth gums. Alginates, carrageenans and cellulose derivatives such as sodium carboxymethyl, methyl, or hydroxy ethyl compounds as appropriate for the intended preparations, surfactants and abrasives may also be included. Alcohols will otherwise be avoided for their known risk factor for oral cancers. In order to decrease dental cavities and add flavor, without using metabolizable sugars, sweetening agents as saccharin, sodium cyclamate, sorbitol, aspartamane and others may be used in concentrations from 0.005 to 5.0% by weight of the total composition, albeit xylitol, vide supra, is preferred.

Lactitol may also be used as a substitute for sucrose in our sugar-free compositions. Lactitol is a disaccharide sugar alcohol derived from lactose, highly water soluble and of low hygroscopicity, making it a suitable non-caloric sweetener for use in solid dosage forms.

A number of compounds may be added to the various liquid compositions of this invention in order to enhance the aromas or tastes of these preparations. These substances may also impart fragrances to the aforementioned. Grapefruit and citrus aroma and flavors have been included in smoking tobacco articles both prior to smoking and on smoking in both the main stream and the side stream smoke. Methyl phenyl pentanol derivatives have been used to augment and enhance aromas, such as in perfumes and colognes. Schreck patented these derivatives for use in tobaccos and tobacco articles in U.S. Pat. No. 4,458,699 (Jul. 10, 1994) which is herein incorporated by reference. Floral, green, weedy, fruity, minty, citrusy, oriental and green pepper-like aroma and taste nuances are well known to those skilled in the art of flavors and fragrances for such compositions as in oral sprays, mouthwashes, mouth rinses, gels, dentifrices and other medicinal, nutritional or breath freshener products.

Wahl and co-workers at the National Institutes of Health taught methods to treat chronic inflammatory diseases in U.S. Pat. No. 5,499,688 (Sep. 12, 1995), which is herein incorporated by reference. They administered effective amounts of nitric oxide scavengers to decrease the amount of putative nitric oxide present at the site of the inflammation. These compounds belonged to complexes with L-arginine, L-canavanine, citrulline and amino guanidine. They note, akin to the argument herein favoring the use of antioxidants to neutralize free radicals. This '688 patent augurs a method for treating gingivitis and periodontitis. Kleinberg in U.S. Pat. No. RE31181 (Mar. 15, 1983), which is also herein incorporated by reference, also teaches arginine and arginine peptides for oral care preparations.

Over the centuries, Chinese herbalists have identified individual herbs that have either beneficial effects on the human body or even therapeutic properties. The National Institute of Health has recently established an agency for research in these so-called alternative therapies.

It is preferred that the antioxidants of the present invention be provided in a form which is as pure as possible. They should be present without noxious lubricants (sand, soaps, talc), fillers, colors, binders, dispersants or like adjuvants sometimes employed as delivery excipients in the aerosol pharmaceutical industry.

Various products may be administered to reduce the viscosity of mucin in sputum. Productive cough is a common symptom. Mucus in the respiratory tract, especially in chronic tobacco smokers as well as other conditions including cystic fibrosis, may be treated with cough syrups and expectorants. Ceramin and Tabachnik described the use of reducing sulfhydryl compounds to decrease the sputum viscosity in patients with pneumonia, chronic bronchitis and cystic fibrosis in U.S. Pat. No. 4,424,216 (January, 1984), which is herein incorporated by reference. They proposed as the preferred sulfhydryl agent WR 2721 to be given orally in capsules of gelatin so that in vivo it may then release free sulfhydryl groups.

Cough suppressants, bronchodilators as well as agents like cysteine, arginine, methionine, taurine, vitamin A and others to reduce mucin viscosity may be added to these compositions. The latter will make sputum more liquid and easier to expectorate for these patients and for chronic tobacco abusers. U.S. Pat. No. 4,927,850, herein incorporated by reference, described methionine in oral or parenteral preparations for ameliorating inflammatory symptoms of respiratory diseases.

As an optional embodiment, the compositions herein described with synergistic antioxidants to combat free radicals in the oropharynx may also contain zinc or zinc compounds. The state of the art of oral care and hygiene has long recognized the value of zinc to neutralize oral malodor and the value of zinc ions for their anti-plaque and anti-calculus properties. Mouth rinses, mouthwashes, gels and dentifrices will thus complement the properties of the xylitol sweetener in oral and dental preventative care.

Various patents have described different zinc compounds and other complexes in oral compositions. Domke and Bergman taught an aqueous zinc-polyamide complex as a solution for control of halitosis, dental care and to decrease the astringency and metallic taste of zinc in the mouth in U.S. Pat. No. 5,587,147 (Dec. 24, 1996), which is herein incorporated by reference. This patent discloses previous documents dealing with zinc salts such as zinc chloride, zinc phenol sulfonate, zinc citrate and other zinc complexes, some of which purportedly also exhibit oral antimicrobial activities. The zinc ion concentrations in these compositions will be at least 0.1 to 3.0 weight percent and these will preferably be in an alkaline pH to avoid demineralization of tooth enamel at acid levels. In any event, these aqueous compositions will not have a pH below 6, and preferably about 7.

Another method of application of the active ingredients in the gum, tablet or lozenge products of the present invention is to incorporate the various anti-oxidants, minerals and amino acids in liposomes or other state of the art encapsulating vehicles, akin to nanospheres, glycospheres and others as used also in topical compositions. Liposomes are lecithin spheres that form an oil protective membrane around the putative active ingredients of the composition. These carriers also deliver the active ingredients locally for their preventive and therapeutic functions as well as systemically through buccal mucosal absorption. Unger and co-workers, in U.S. Pat. No. 5,580,575 (Dec. 3, 1996), which is herein incorporated by reference, have taught therapeutic drug delivery systems comprising gas-filled liposomes which encapsulate the active preparation. Earlier, Chakrabarti and associates, in U.S. Pat. No. 5,380,531 (Jan. 10, 1995), which is also herein incorporated by reference, disclosed preparations comprising a lipid and a modified peptide for similar uses of amino acids and peptides into liposomes. Knight et al. (U.S. Pat. No. '388) has taught about small particle aerosol liposomes and liposome combinations for medical delivery uses.

I claim:

1. A composition for reducing free radical damage induced by tobacco products and environmental pollutants comprising, as active ingredients, reduced glutathione and a source of selenium selected from the group consisting of elemental selenium, selenomethionine and selenocysteine, said active ingredients being combined with suitable carriers and flavorings for their intra-oral administration as gels, lozenges, tablets and gums in concentrations for reducing free radical damage induced by tobacco products and other environmental pollutants to the oral cavity, pharynx and upper respiratory tract of a user and secondary smokers.

2. The composition of claim 1 wherein each of said gels, lozenges, tablets and gums contains at least approximately 0.5 mg. of said reduced glutathione.

3. The composition of claim 1 wherein said gels, lozenges, tablets and gums contains at least approximately 5 mcgm. of said source of selenium.

4. The composition of claim 1 wherein said gels, lozenges, tablets and gums further contain at least approximately 15 mg of vitamin C as ascorbic acid or as a derivative of ascorbic acid.

5. The composition of claim 1 wherein said gels, lozenges, tablets and gums further contain at least approximately 10 IU of vitamin E as alpha tocopherol.

6. The composition of claim 1 wherein said gels, lozenges, tablets and gums further contain superoxide dismutase.

7. The composition of claim 1 wherein said gels, lozenges, tablets and gums further contain vitamin A.

8. The composition of claim 1 wherein said gels, lozenges, tablets and gums further contain beta carotene.

9. The composition of claim 1 wherein said gels, lozenges, tablets and gums further contain at least one amino acid selected from the group consisting of cysteine, methionine, taurine and arginine.

10. The composition of claim 1 wherein said gels, lozenges, tablets and gums further contain a zinc salt.

11. The composition of claim 10 wherein said zinc salt comprises zinc glutonate.

12. A gum for reducing free radical damage induced by tobacco products and environmental pollutants comprising, as active ingredients, reduced glutathione, a source of selenium selected from the group consisting of elemental selenium, selenomethionine and selenocysteine, combined in a suitable carrier containing flavorings to produce a chewable gum in concentrations for reducing free radical damage induced by these tobacco products and other environmental pollutants to the oral cavity, pharynx and upper respiratory tract of a user and secondary smoker.

13. The gum of claim 12 wherein said gum further includes a gum base comprising approximately 40 to 60% by weight of the gum composition.

14. The gum of claim 13 wherein said gum base comprises an elastomer, a polyvinyl acetate polymer, an acetylated monoglyceride, a wax with melting point below approximately 60° C., an elastomer solvent, a plasticizer and a filler.

15. The gum of claim 12 comprising at least approximately 0.1 mg reduced glutathione, 20 mcgm of said source of selenium and further comprising at least approximately 10 mg ascorbic acid, 25 IU vitamin E and 1.0 mg of a cysteine selected from the group consisting of L-cysteine and N-acetyl cysteine.

16. The gum of claim 12 further comprising a sweetener selected from the group consisting of xylitol, lactitol, sucrose, lactose and a saccharide.

17. A lozenge for reducing free radical damage induced by tobacco products and environmental pollutants comprising as active ingredients, reduced glutathione and a source of selenium selected from the group consisting of elemental selenium, selenomethionine and selenocysteine combined in a suitable carrier to enable the lozenge to slowly dissolve in a user's mouth releasing said active ingredients in concentrations for reducing free radical damage induced by tobacco products and other environmental pollutants to the oral cavity, pharynx and upper respiratory tract of a user and secondary smoker.

18. The lozenge of claim 17 wherein said lozenge is sized so that a user would be administered said active ingredients in from one to four lozenges to supply a recommended daily allowance of said active ingredients.

19. The lozenge of claim 18 wherein said lozenge is sized so that said one to four lozenges are sized to provide a user with approximately at least 40 mg reduced glutathione, 25 mcgm selenomethionine, 30 mg ascorbic acid, 15 IU alpha tocopherol, 2500 IU retinyl acetate and 10 mg L-cysteine, daily.

20. A chewable tablet for reducing free radical damage induced by tobacco products and environmental pollutants comprising as active ingredients, reduced glutathione and a source of selenium selected from the group consisting of elemental selenium, selenomethionine and selenocysteine combined with a suitable carrier to enable the chewable tablet to be masticated by teeth of the user releasing said active ingredients in concentrations for reducing free radical damage induced by tobacco products and other environmental pollutants to the oral cavity, pharynx and upper respiratory tract of a user and secondary smoker.

21. The chewable tablet of claim 20 wherein said chewable tablet is sized so that a user would be administered said active ingredients in from one to four chewable tablets to supply a recommended daily allowance of said active ingredients.

22. The chewable tablet of claim 21 wherein said chewable tablet is sized so that said one to four chewable tablets are sized to provide a user with approximately at least 40 mg reduced glutathione, 25 mcgm selenomethionine, 30 mg ascorbic acid, 15 IU alpha tocopherol, 2500 IU retinyl acetate and 10 mg L-cysteine, daily.

23. A method for reducing free radical damage induced by tobacco products and environmental pollutants comprising administering in a suitable carrier, in concentrations for effectively reducing said free radical damage to the oral cavity, pharynx and upper respiratory tract of a user a combination of reduced glutathione and a source of selenium as a member selected from the group consisting of elemental selenium, selenomethionine and selenocysteine in the form of a gel, gum, lozenge or chewable tablet.

24. The method of claim 23 wherein each of said gels, lozenges, tablets and gums contains at least approximately 0.5 mg. of said reduced glutathione.

25. The method of claim 23 wherein said gels, lozenges, tablets and gums contains at least approximately 5 mcgm. of said source of selenium.

26. The method of claim 23 wherein said gels, lozenges, tablets and gums further contain at least approximately 15 mg of vitamin C as ascorbic acid or as a derivative of ascorbic acid.

27. The method of claim 23 wherein said gels, lozenges, tablets and gums further contain at least approximately 10 IU of vitamin E as alpha tocopherol.

28. The method of claim 23 wherein said gels, lozenges, tablets and gums further contain superoxide dismutase.

29. The method of claim 23 wherein said gels, lozenges, tablets and gums further contain vitamin A.

30. The method of claim 23 wherein said gels, lozenges, tablets and gums further contain beta carotene.

31. The method of claim 23 wherein said gels, lozenges, tablets and gums further contain at least one amino acid selected from the group consisting of cysteine, methionine, taurine and arginine.

32. The method of claim 23 wherein said gels, lozenges, tablets and gums further contain a zinc salt.

33. The method of claim 32 wherein said zinc salt comprises zinc glutonate.

\* \* \* \* \*